(12) United States Patent
Pounds

(10) Patent No.: US 8,058,464 B2
(45) Date of Patent: Nov. 15, 2011

(54) ISOTOPICALLY LABELED CHEMICALLY STABLE REAGENTS AND PROCESS FOR THE SYNTHESIS THEREOF

(75) Inventor: Jerry Scot Pounds, Milton, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 631 days.

(21) Appl. No.: 10/559,047

(22) PCT Filed: May 28, 2004

(86) PCT No.: PCT/US2004/016898
§ 371 (c)(1),
(2), (4) Date: Mar. 28, 2006

(87) PCT Pub. No.: WO2004/108636
PCT Pub. Date: Dec. 16, 2004

(65) Prior Publication Data
US 2006/0205953 A1    Sep. 14, 2006

Related U.S. Application Data

(60) Provisional application No. 60/320,238, filed on May 30, 2003.

(51) Int. Cl.
*C07C 309/73* (2006.01)
(52) U.S. Cl. ........................................ 558/56
(58) Field of Classification Search ............ 558/56
See application file for complete search history.

(56) References Cited

U.S. PATENT DOCUMENTS

| 4,269,777 A | 5/1981 | De Luca et al. |
| 6,713,044 B2 | 3/2004 | Martinez et al. |

FOREIGN PATENT DOCUMENTS

JP    56-500538 T    4/1981

OTHER PUBLICATIONS

Lee et al. "Substituent Effects on Transition-state Structures for Dissociative and Associative Sn2 Reactions" J. Chem. Soc. Perkin Trans. 1991, pp. 1741-1746.*
Gragerov, CAS Accession No. 1955:63263.*
Llewellyn et al. "Some Deuterium Isotope Effects: I. Water Solvolysis of Methyl-d3 Esters" Canadian Journal of Chemistry, 1960, vol. 38, pp. 222-232.*
Bailey et al. CAS Accession No. 1989:212048, 1989.*
Nefedov et al. Beilstein Registry No. 4368300, 1980.*
Nefedov et al. Beilstein Registry No. 4367300, 1980.*
Pounds, Scot Preparation of carrier-free [methyl-3H] methyl nosylate and its use as a radiochemically-stable methylating reagent; Proceedings of the International Symposium, Boston, MA Jun. 1-5, 2003; XP002401240.
Pounds, Scot Preparation of carrier-free [methyl-3H] methyl nosylate and its use as a radiochemically-stable methylating reagent; Proceedings of the International Symposium, Boston, MA Jun. 1-5, 2003; XP002401241.
Bellstein Institut Zur Foerderung Der Chemischen Wissenschaften, Frankfurt AM Main, J. Chem Soc. Perkin Trans 2, 1991 pp. 1741-1746; XP002401242.
Beilstein Institut Zur Foerderung Der Chemischen Wissenschaften, Frankfurt AM Main, J. Chem Soc. Perkin Trans 1, vol. 12 1984, pp. 2919-2925; XP002401243.
Beilstein Institut Zur Foerderung Der Chemischen Wissenschaften, Frankfurt AM Main, J. Chem Heterocycl. Compd. vol. 20, No. 6, 1984 pp. 637-642; XP002401244.
Beilstein Institut Zur Foerderung Der Chemischen Wissenschaften, Frankfurt AM Main, J. Chem Soc. Perkin vol. 77, 1955 pp. 5515-5517; XP002401245.
Beilstein Institut Zur Foerderung Der Chemischen Wissenschaften, Frankfurt AM Main, J. Chem Soc. Perkin vol. 99, 1977 pp. 851-857; XP002401246.
Beilstein Institut Zur Foerderung Der Chemischen Wissenschaften, Frankfurt AM Main, Can J. Chem vol. 32, 1954 p. 1; XP002401247.
Beilstein Institut Zur Foerderung Der Chemischen Wissenschaften, Frankfurt AM Main, Can J. Chem, USSR, vol. 34, 1956 p. 179; XP002401248.
Beilstein Institut Zur Foerderung Der Chemischen Wissenschaften, Frankfurt AM Main, J. Org. Chem USSR, vol. 16, 1980 pp. 1944-1946; XP002401249.
Bellstein Institut Zur Foerderung Der Chemischen Wissenschaften, Frankfurt AM Main, J. Org. Chem USSR, vol. 16, 1980 pp. 1944-1946; XP002401250.
Beilstein Institut Zur Poerderung Der Chemischen Wissenschaften, Frankfurt AM Main, J. Phys. Chem, vol. 88, No. 9, 1984 pp. 1701-1706; XP002401251.
Beilstein Institut Zur Foerderung Der Chemischen Wissenschaften, Frankfurt AM Main, J. AM. Chem Soc. vol. 103, No. 1, 1981 pp. 36-39; XP002401252.
Beilstein Institut Zur Foerderung Der Chemischen Wissenschaften, Frankfurt AM Main, J. Chem Soc. Perkin Trans., 19804, pp. 2902-2913; XP002401253.
Beilstein Institut Zur Foerderung Der Chemischen Wissenschaften, Frankfurt AM Main, Biosci. Biotechnol. Biochem, vol. 60, No. 9, 1996, pp. 1460-1463; XP002401254.
Beilstein Institut Zur Foerderung Der Chemischen Wissenschaften, Frankfurt AM Main, Chem. Pharm. Bull., vol. 44, No. 6, 1996, p. 12481249; XP002401255.

(Continued)

*Primary Examiner* — Joseph Kosack
(74) *Attorney, Agent, or Firm* — Gifford, Krass, Sprinkle, Anderson & Citkowski, P.C.

(57) ABSTRACT

A radioisotope labeled reagent includes a compound having the general formula (I) where a in each occurrence independently is a carbon mass number between 11 and 14 inclusive, b in each occurrence independently is a hydrogen mass number between 1 and 3 inclusive, such that a in each occurrence is not 12 simultaneously with b in each occurrence being 1; L is a leaving group $R^1SO_2-O-$, $R^1-S-$, $^{12}C^1H_3$ $(^{12}C^1H_2)_n-S-R^1C(O)O-$, NC—, $(R^1)_3P-$, XMg— and Li—, where n is an integer between 0 and 3 inclusive, where X is chloro, bromo or iodine, where $R^1$ is H, aryl, a substituent containing aryl, $C_1$-$C_{20}$ alkyl, a substituent containing $C_1$-$C_{20}$ alkyl, $C_2$-$C_{20}$ alkenyl, a substituent containing $C_2$-$C_{20}$ alkenyl, $C_2$-$C_{20}$ alkynyl, and a substitute containing $C_2$-$C_{20}$ alkynyl with the proviso that when n is 0, a is 13 and b is 2 and $R^1$ in R1-S is not aryl.

$$L\text{-}(^aC^bH_2)_n{}^aC^bH_3 \qquad (I)$$

3 Claims, No Drawings

OTHER PUBLICATIONS

Ault, Bruce S., Infrared matrix isolation study of magnesium metal atom reactions. Journal of the American Chemical Society, 1980, p. 3491, XP002401219.

Mayo, D. W. et al., The application of resolution enhancement techniques to the study of factors affecting group frequencies,Spectrochmica Acta, Part A: Molecular and Biololecular Spectroscopy, 1985, pp. 355-356; XP002401220.

Sy, L.-K. e al., Syntheses of dihydroertemisinic acid and dihydro-epi-deoxyarteannuin B Incorporating a stable isotope label at the 15-position for studies into the biosynthesis of artemisinin, p. 8498, 8506, col. 1, XP002401121.

Beilstein Institut Zur Poerderung Der Chemischen Wissenschaften, Frankfurt AM Main, Synth. Commun., vol. 25, No. 17, 1995 pp. 2685-2694. XP002401256.

Bellsteln Institut Zur Poerderung Der Chemischen Wissenschaften, Frankfurt AM Main, J. Labelled Compd, Radlopherm vol. 45, No. 5, 2002, pp. 401-406; XP002401257.

Scot Pounds; Preparation of carrier-free [methyl-3H] methyl nosylate and its use as a radiochemically-stable methylating reagent; Database Accession No. 2004:859485; Synthesis and Applications of Isotopically Labelled Compounds, Proceedings of the International Symposium; 8th, Boston, MA; United States, (2004); XP-002401240.

Scot Pounds; Preparation of carrier-free [methyl-3H] methyl nosylate and its use as a radiochemically-stable methylating reagent; Database Accession No. 2004:859381; Synthesis and Applications of Isotopically Labelled Compounds, Proceedings of the International Symposium; 8th, Boston, MA; United States, (2004); XP-002401241.

Beilstein Institut Zur Foerderung Der Chemischen Wissenschaften; Frankfurt AM Main, DE: Database Accession No. 4875789; J. Chem. Soc. Perkin Trans. 2, 1991; XP-002401242.

Beilstein Institut Zur Foerderung Der Chemischen Wissenschaften; Frankfurt AM Main, DE: Database Accession No. 2379871; J. Chem. Soc. Perkin Trans. 1, vol. 12, 1984; XP-002401243.

Beilstein Institut Zur Foerderung Der Chemischen Wissenschaften; Frankfurt AM Main, DE: Database Accession No. 4682440; Chem. Heterocycl. Compd., vol. 20, No. 6, 1984; XP-002401244.

Beilstein Institut Zur Foerderung Der Chemischen Wissenschaften; Frankfurt AM Main, DE: Database Accession No. 2651782; J. Am. Chem. Soc., vol. 77, 1955; XP-002401245.

Beilstein Institut Zur Foerderung Der Chemischen Wissenschaften; Frankfurt AM Main, DE: Database Accession No. 2861936; J. Am. Chem. Soc., vol. 99, 1977; XP-002401246.

Beilstein Institut Zur Foerderung Der Chemischen Wissenschaften; Frankfurt AM Main, DE: Database Accession No. 1753621; Can. J. Chem., vol. 32, 1954; XP-002401247.

Beilstein Institut Zur Foerderung Der Chemischen Wissenschaften; Frankfurt AM Main, DE: Database Accession No. 1762191; Can. J. Chem., vol. 34, 1956; XP-002401248.

Beilstein Institut Zur Foerderung Der Chemischen Wissenschaften; Frankfurt AM Main, DE: Database Accession No. 4368300; J. Org. Chem. USSR, vol. 16, 1980; XP-002401249.

Beilstein Institut Zur Foerderung Der Chemischen Wissenschaften; Frankfurt AM Main, DE: Database Accession No. 4367300; J. Org. Chem. USSR, vol. 16, 1980; XP-002401250.

Beilstein Institut Zur Foerderung Der Chemischen Wissenschaften; Frankfurt AM Main, DE: Database Accession No. 1927100; J. Phys. Chem., vol. 88, No. 9,1984; XP-002401251.

Beilstein Institut Zur Foerderung Der Chemischen Wissenschaften; Frankfurt AM Main, DE: Database Accession No. 4961534; J. Am. Chem. Soc., vol. 103, No. 1, 1981; XP-002401252.

Beilstein Institut Zur Foerderung Der Chemischen Wissenschaften; Frankfurt AM Main, DE: Database Accession No. 4964579; J. Am. Chem. Soc. Perkin Trans.; XP-002401253.

Beilstein Institut Zur Foerderung Der Chemischen Wissenschaften; Frankfurt AM Main, DE: Database Accession No. 3560149; J. Biosci. Biotechnol. Biochem., vol. 60, No. 9; 1996.; XP-002401254.

Beilstein Institut Zur Foerderung Der Chemischen Wissenschaften; Frankfurt AM Main, DE: Database Accession No. 7631896; Chem. Pharm. Bull., vol. 44, No. 6; 1996.; XP-002401255.

Bruce S. Ault; Infrared Matrix Isolation Study of Magnesium Metal Atom Reactions. Spectra of an Unsolvated Grignard Species; Journal of the American Chemical Society; pp. 3480-3484; XP-002401219.

D.W. Mayo et al.; The application of resolution enhancement techniques to the study factors affecting group frequencies-I. Coupling of symmetric methyl deformation frequencies in o-xylene; Spectrochimica Acta, vol. 41A I, 1/2; pp. 355-357; 1985; XP-002401220.

Lai-King Sy et al.; Syntheses of dihydroartemisinic acid and dihydro-epi-deoxyarteannuin B incorporating a stable isotope label at the 15-position for studies into the biosynthesis of artemisinin; Tetrahedron 57; (2001); pp. 8495-8510; XP-002401221.

Beilstein Institut Zur Foerderung Der Chemischen Wissenschaften; Frankfurt AM Main, DE: Database Accession No. 7306630; Synth. Commun., vol. 25, No. 17; 1995.; XP-002401256.

Beilstein Institut Zur Foerderung Der Chemischen Wissenschaften; Frankfurt AM Main, DE: Database Accession No. 7306630; J. Labelled Compd.; XP-002401257.

Nefedov et al.; Beilstein Registry No. 4368300, 1980.

E.M. Zippi et al.; Preparation and use of Lithium Tritide and Lithium Trimethoxyborotritide; Synthetic Communications; vol. 25; No. 17; 1995; pp. 2685-2693.

Kjell Rynefors et al.; Extension of Total Angular Momentum Representation in Energy Space; Chemical Physics Letters; vol. 122; 1985; pp. 2-6E.

Graeme Milligan et al; Use of [3H] Triphenylmethylphosphonium Cation for Estimating Membrane Potential in Neuroblastoma Cells; Journal of Neurochemistry; pp. 1515-1521.

Richard S. P. Hsi et al.; Biosynthesis of Tritium, Deuterium and Carbon-13 Labeled Cycloheximide; Journal of Labelled Compounds and Radiopharmaceuticals; vol. XVII; No. 5; 1979; pp. 613-626.

C.A. Wachtmeister et al; The Synthesis of Some Tritium-Labelled Mutagenic Alkyl Alkanesulfonates; Acia Chem.; 1966, No. 3; pp. 909-910.

* cited by examiner

ISOTOPICALLY LABELED CHEMICALLY STABLE REAGENTS AND PROCESS FOR THE SYNTHESIS THEREOF

RELATED APPLICATION

This application is a U.S. national phase application under 371 of PCT Application No. PCT/US2004/016898 filed May 28, 2004, which claims priority of U.S. Provisional Patent Application Ser. No. 60/320,238 filed May 30, 2003, which is incorporated herein by reference.

FIELD OF THE INVENTION

The present invention relates in general to reagents having isotopic labels and in particular to tritiated reagents having greater stability than alkyl halides.

BACKGROUND OF THE INVENTION

Alkyl halides are versatile alkylating agents in organic chemistry. Methyl halides are particularly popular as alkylating agents. Representative of the methyl halides is methyl iodide, which in a pure state is a clear liquid that over time becomes brown as a result of decomposition to form various iodine-containing species. Methyl iodide is often stabilized through the addition of a solid metal such as mercury or copper to the storage vessel. As alkyl halides including methyl iodide are susceptible to actinic degradation and free radical decomposition, alkyl halide storage is often problematic. Nonetheless, aged alkyl halides are readily restored to usable form through a distillation process.

The handling of isotopically enriched alkyl halides is made all the more difficult by radioisotope emissions creating free radicals that speed the chemical decomposition of the alkyl halide. Distillation to purify usable alkyl halides from a decomposing isotopically enriched alkyl halide is both technically challenging to perform and highly wasteful of radioisotopes.

Owing to the complexities of handling radioisotopes, isotopically labeled reagents tend to be small molecules that can be synthesized and used quickly. [Methyl-$^3$H]methyl iodide is a common methylating reagent used in the synthesis of methyl-labeled radiochemicals. Unfortunately, the rapid degradation of tritiated methyl iodide and other isotope-enriched alkyl halides means that these reagents must be used rapidly after synthesis. The requirement of rapid usage of isotopically labeled alkyl halides entails a scheduled batch production of the reagent followed by numerous reagent consumptive reactions being performed thereafter. The net result is that labeling reactions cannot be efficiently performed but instead are tied to the schedule of alkyl halide production. Additionally, an excess of isotopically enriched alkyl halide is necessarily produced to preclude the possibility of performing a second batch production to account for any shortfall. The resulting excess production of isotopically enriched alkyl halide is wasteful of materials and increases the waste disposal volume. Thus, there exists a need for an isotopically enriched alkylating reagent that has a longer shelf life than the corresponding alkyl halide without loss of specific isotope activity.

SUMMARY OF THE INVENTION

A radioisotope labeled reagent includes a compound having the general formula (I), $$L\text{-}(^aC^bH_2)_n{}^aC^bH_3 \tag{I}$$

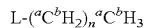

where a in each occurrence independently is a carbon mass number between 11 and 14 inclusive, b in each occurrence independently is a hydrogen mass number between 1 and 3 inclusive, such that a in each occurrence is not 12 simultaneously with b in each occurrence being 1; L is a leaving group $R^1SO_2$—O—, $R^1$—S—, $^{12}C^1H_3(^{12}C^1H_2)_n$—S—$R^1C$(O)O—, NC—, $(R^1)_3P$—, XMg— and Li—, where n is an integer between 0 and 3 inclusive, where X is chloro, bromo or iodine, where $R^1$ is H, aryl, a substituent containing aryl, $C_1$-$C_{20}$ alkyl, a substituent containing $C_1$-$C_{20}$ alkyl, $C_2$-$C_{20}$ alkenyl, a substituent containing $C_2$-$C_{20}$ alkenyl, $C_2$-$C_{20}$ alkynyl, and a substitute containing $C_2$-$C_{20}$ alkynyl with the proviso that when n is 0, a is 13 and b is 2 and $R^1$ in $R^1$—S is not aryl.

A process for preparing a compound of Formula I includes reacting an isotope enriched methyl halide, where L is a leaving group representative of $^aC^bH_3(^aC^bH_2)_nX$ with $[L]^{y-}M_p^{z+}$ or Mg, M is a metal ion or onium ion, Z+ is a cationic valency of M, Y− is an anionic valency of L, p is the absolute value of the anionic valency divided by the cation valency; preferably under anhydrous conditions in an aprotic solvent. Protic solvent and small amounts of water are tolerated in certain synthetic schemes.

A method of isotopically alkylating a target molecule involves mixing the target molecule under reaction conditions with an effective amount of compound according to Formula I. The compound of Formula I is useful in isotopically labeling a target molecule and has the advantage of extended storage stability relative to the corresponding methyl iodide reagent.

A commercial package includes a compound of Formula I together with instructions for the use thereof as an isotopic labeling reagent. The enhanced chemical stability of a compound of Formula I affords the possibility of performing isotopic labeling reactions remote from the reagent synthesis.

DETAILED DESCRIPTION OF THE PREFERRED EMBODIMENTS

The present invention has utility as an isotopic labeling reagent having superior storage properties as compared to the corresponding alkyl halide. The labeling reagents according to the present invention are operative to introduce carbon-11 [$^{11}$C], carbon-12 [$^{12}$C], carbon-13 [$^{13}$C] and carbon-14 [$^{14}$C]. Independent of whether the methyl carbon is a radioisotope, the three hydrogen atoms making up a methyl group are 3 hydrogen-1 [$^1$H$_3$], 3 hydrogen-2 [$^2$H$_3$] or 3 hydrogen-3 [$^3$H$_3$] with the condition that at least one of the carbon or the three hydrogens of the methyl group are naturally occurring minor constituent isotopes. Preferably, methylene (—$^aC^bH_2$—) groups in higher alkyls share the isotopic identity of the thermal methyl group. As used herein, deuterium is appreciated to be synonymous with hydrogen-2 and tritium synonymous with $^3$H. While according to the present invention all three hydrogen atoms that compose the methyl group are isotopically identical, it is appreciated that isotopically mixed hydrogen atoms are operative to form a methyl group. An isotope labeled reagent is a compound having a general formula $$L\text{-}(^aC^bH_2)_n{}^aC^bH_3 \tag{I}$$

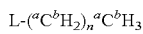

where a in each occurrence independently is a carbon atom mass number of between 11 and 14 inclusive, b in each occurrence independently is a hydrogen atom mass number of between 1 and 3 inclusive, and at least one of a and b is a naturally occurring minor isotope constituent. An "isotope" for carbon is defined herein to include instances where the majority of carbon atoms have a carbon atomic mass number of other than carbon-12. An enriched isotope of hydrogen has as the majority hydrogen atomic mass number a value of 2 or 3. Preferably, the carbon atomic mass number is 12 and all the hydrogen atomic mass numbers are 3.

The leaving group L is selected to represent a chemically stable leaving group upon reaction with a target molecule nucleophile. The leaving group L is representative of: $R^1SO_2$—O—, $R^1$—S—, $^{12}C^1H_3(^{12}C^1H_2)_n$—S—, $R^1C(O)$O—, NC—, $(R^1)_3P$—, XMg— and Li—. $R^1$ is hydrogen, aryl, a substituent containing aryl, $C_1$-$C_{20}$ alkyl, a substituent containing $C_1$-$C_{20}$ alkyl, $C_2$-$C_{20}$ alkenyl, a substituent containing $C_2$-$C_{20}$ alkenyl, $C_2$-$C_{20}$ alkynyl, and a substituent containing $C_2$-$C_{20}$ alkynyl. It is appreciated that the substituent, if present, is non-reactive towards intramolecular reaction within the compound. An aryl group according to the present invention is a monovalent monocyclic or bicyclic aromatic hydrocarbon radical of 6 to 10 ring atoms and illustratively includes naphthyl, a substituent containing naphthyl, phenyl, and a substituent containing phenyl with the proviso that a is not 13 and b is not 2 in the instance when the leaving group L is the mercapto aryl $R^1$—S—. $C_1$-$C_{20}$ alkyl, $C_2$-$C_{20}$ alkenyl and $C_2$-$C_{20}$ alkynyl leaving groups operative herein include linear, branched, cyclic and bicyclic species. A substituent operative herein to modify an aryl, alkyl, alkenyl, or alkynyl replaces a hydrogen bonded to a carbon atom with each substituent independently being selected from alkyl, amino, cycloalkyl, halo, nitro, cyano, —$OR^2$, acyl, and —$COOR^3$. Alkyl substituents are $C_1$-$C_6$ and preferably, $C_1$-$C_4$. Operative alkyl substituents illustratively include methyl, ethyl, n-propyl, isopropyl, butyl, isobutyl, terbutyl, pentyl, isopentyl, and hexyl. A cycloalkyl substituent operative herein is a $C_5$ or $C_6$ cyclopentyl or cyclohexyl species. A hetero cycloalkyl operative herein is selected from furanyl, tetrahydrofuranyl, epoxi, tetrahydropyranyl, dioxynyl, thiacyclopentyl, azeridyl pyrolidyl, piperadyl, morpholyl, and alkyl substituted forms thereof. Halo substituents operative herein are selected from fluoro, chloro, bromo and iodo. A substituent amino group is selected from $NH_2$, $NHRR^4$ or $NR^4R^5$. $R^2$ is selected from hydrogen, $C_1$-$C_6$ alkyl, $C_5$ or $C_6$ cycloalkyl, a heterocycloalkyl as described above, or a substituent containing phenyl. $R^3$ is hydrogen or $C_1$-$C_6$ alkyl. $R^4$ and $R^5$ in each occurrence are independently selected from $C_1$-$C_6$ alkyl, aryl as described above, $C_1$-$C_6$ alkoxy, and $C_6$ phenoxy.

Specific examples of isotopically labeled reagents according to the present invention include methyl sulfonic acid, methyl tosylate, methyl mesylate, methyl nosylate, dimethyl thioether, terbutyl methyl thioether, methyl benzoate, methilide triphenyl phosphene, methyl magnesium chloride, and methyl lithium. Additionally, it is appreciated that substituents of a leaving group L optionally incorporate a dye moiety illustratively including cyanine, rhodamine or other conjugated aromatic functionality to render inventive reagent an isotopic, as well as a spectroscopic labeling compound. It is further appreciated that each of the reagent compounds produced according to the present invention, while having superior stability and handling properties as compared to isotopically labeled methyl halides, has limitations as to the reactions in which it is operative. By way of example, methyl magnesium halides and methyl lithium are operative in aqueous environments only to form isotopically labeled methane whereas in anhydrous environments are suitable to perform labeling reactions well known to the art. Methylide phosphenes are operative in performing Wittig reactions, while in general inventive compounds are useful in performing nucleophilic substitution labeling reactions.

A process for preparation of a compound of Formula I is summarized by the following reaction:

(IIA)

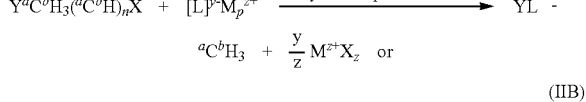

or (IIB)

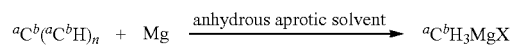

where L is the leaving group described with respect to the compound of Formula I with the exclusion of magnesium which does not react by a metathesis reaction but instead is additive to form the resulting methyl Grignard reagent. And in the case of methyl lithium, the reaction IIA is satisfied by $[L]^{Y-}$ being $Li^{1-}$. M is a metal ion or onium ion. M is a lithium ion, sodium ion, potassium ion, magnesium ion, calcium ion, barium ion, cesium ion, silver ion, zinc ion, copper ion, cobalt ion, iron ion, nickel ion, manganese ion, titanium ion, lead ion, chromium ion, vanadium ion, ruthenium ion, yttrium ion, lanthanoid ion, actinoid ion, tetrabutylammonium ion, tetraethylammonium ion, tetramethylammonium ion, triethylmethylammonium ion, triethylammonium ion, pyridinium ion, imidazolium ion, hydrogen ion, tetraethylphosphonium ion, tetramethylphosphonium ion, tetraphenylphosphonium ion, triphenylsulfonium ion, or triethylsulfonium ion. Preferably, the metal ion M is selected to produce a stable metal halide that facilitates separation of the inventive compound of Formula I therefrom. Preferred metal ions include silver and other transition metals. X as per the compound of Formula I is chloride, bromide or iodide. As shown in the general Formula IIA, the valency of $M^{Z+}$ cation is preferably from 1 to 3, inclusive. In instances where the valency of $M^{Z+}$ is greater than 3, dissolution of ionic metal complex in solvent tends to occur as a result of increases in crystal lattice energy. As a result, in a more preferred embodiment, the valency of $M^{Z+}$ is 1. As shown in the general Formula IIA, the valency Y– of L is similarly preferably from 1 to 3 with a valency of 1– being most preferred. P is the absolute value of the anionic valency to the Y– divided by the cation valency Z+ and thereby provide net charge neutrality.

Methyl iodide for use in reaction Formulas IIA and IIB are produced by established techniques. $^{12}C^3H_3I$ is produced by a well-established technique. Dass, Desmond V.; Dempsey, Victor J.; Martin, R. Wayne; Odell, Allan L., Journal of Labelled Compounds and Radiopharmaceuticals (1987), 24(5), 517-20; Liu, Yu-Ying; Chen, Journal of Labelled Compounds & Radiopharmaceuticals (1996), 38(1), 71-6, and Schwob, R.; Wuersch, J., Journal of Labelled Compounds and Radiopharmaceuticals (1978), 14(3), 355-60. $^{11}C^1H_3$ methyl iodide is produced with the well-established reaction of carbon-11 dioxide with lithium aluminum hydride and subsequent hydrolysis with hydroiodic acid. $^{13}C$ with 1, 2 or 3 deuterium atoms present in the methyl group are produced as detailed in U.S. Pat. No. 6,713,044 B2. Powdered magnesium and reagents of the form $[L]^{Y-}M^{C+}_p$ according to the present invention are conventional to the art and in most cases commercially available reagents. The reaction conditions to perform the reaction of Formulas IIA and IIB in order to produce a compound according to Formula I are known to the art for a specific reaction involving an alkyl halide and are in general characterized by reaction in an aprotic solvent under anhydrous conditions. Further guidance as to reaction conditions is found with reference to Grignard reagent synthesis and the Williamson ether synthesis. The reaction process of Formulas IIA and IIB yield a product that has greater chemical stability than the corresponding alkyl halide while preserving the isotopic character of the alkyl halide. The resulting inventive reagents are further characterized by being nonvolatile and of lesser toxicity than the corresponding alkyl halide.

A commercial package according to the present invention includes a compound of Formula I, preferably in purified form, together with instructions for the use of the compound as an isotopic labeling reagent. One of skill in the art will appreciate that those compounds of Formula I that represent esters of strong acids are well suited as reagents for labeling nucleophiles by way of an $S_N2$ reaction mechanism. Alternatively, Grignard reagents and alkyl lithium reagents are well suited for the production of ketones from carboxylic acids and carboxylic acid derivatives illustratively including amides and esters. In the case of esters, it is appreciated that the resulting ketone in the presence of a Grignard reagent is unstable resulting in a methylated tertiary alcohol.

The invention is better understood with respect to the following examples. These examples are given as being illustrative of the present invention and are not to be construed as limiting the invention either in spirit or in scope as many modifications both in materials and methods will be apparent to those skilled in the art upon reading the same. While the following examples all pertain to $^{12}C^3H_3I$ as a starting material, it is appreciated that other isotopically enriched alkyl halides according to the present invention are equally operative herein.

Example 1

Typical Preparation of [Methyl-$^{12}C^3H$] Methyl Para-toluenesulfonate (III)

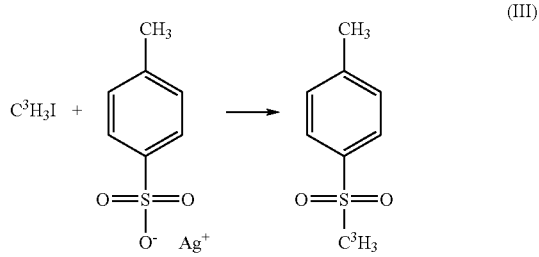

0.4 mmol (35 Ci, carrier-free) of $^{12}C^3H_3I$ is sealed into a glass reaction bulb with silver tosylate (140 mg, 0.5 mmol) and 5 ml of anhydrous acetonitrile. The reaction is heated to 80° C. overnight. Labiles are removed, and the residue dissolves in ethyl acetate. The yield is 30 Ci (85%) of [Methyl-$^{12}C^3H$]methyl para-toluenesulfonate (III). The labeled material and authentic cold standard comigrated on thin layer chromatography (TLC), (Whatman LK6DF, hexane-ethyl acetate, 10:3, $R_f$=0.5). Stored at 600 mCi/ml in ethyl acetate at 25° C., the radiochemical purity as determined by TLC as above is unchanged after 20 days.

Example 2

Synthesis of L-[N-Methyl-$^{12}C^3H$] Quinuclidinyl Benzilate Methyl Chloride (IV) with [Methyl-$^{12}C^3H$]Methyl Para-toluenesulfonate (III)

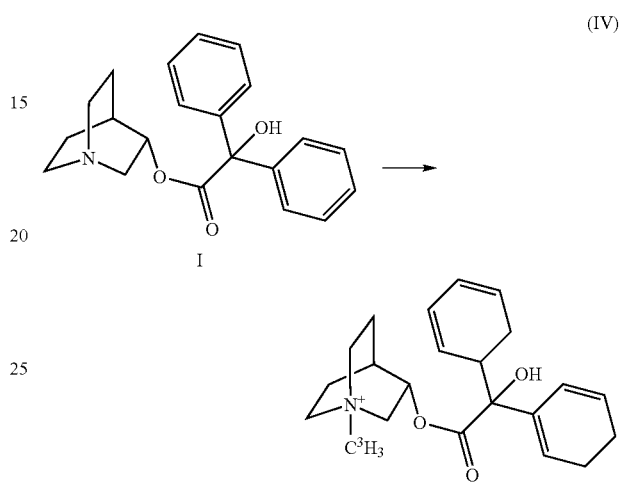

600 mCi (0.0073 mmol) of [methyl-$^{12}C^3H$]methyl para-toluenesulfonate (III) and 10 mg (0.03 mmol) of R-(−)-3-quinuclidinyl benzilate are stirred in 2 ml of methanol at room temperature overnight. TLC of the reaction (silica gel GHLF, n-butanol-acetic acid-water, 4:1:1) shows only product and unreacted tosylate. The whole is purified on HPLC (Zorbax SB-C8, methanol-1% TEAA pH4, gradient) to give after addition of a chloride source L-[N-methyl-$^{12}C^3H$] quinuclidinyl benzilate methyl chloride (IV). The specific activity is determined to be 82.0 Ci/mmol by mass spectral analysis, and the radiochemical purity determined by HPLC as above is 99%.

Example 3

Typical Preparation of [Methyl-$^3H$]Methyl Para-nitrobenzenesulfonate (V)

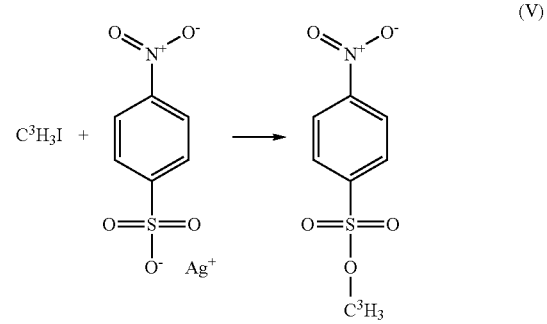

0.14 mmol (12 Ci, carrier-free) of $^{12}C^3H_3I$ is sealed into a glass reaction bulb with silver nosylate (62 mg, 0.2 mmol) and 5 ml of anhydrous acetonitrile. The reaction is heated to 80° C. overnight. Labiles are removed, and the residue dissolves in ethyl acetate. The yield is 6.16 Ci (51%) of [methyl-$^{12}C^3H$]methyl para-nitrobenzenesulfonate (V). The labeled material and authentic cold standard comigrated on TLC (Whatman LK6DF, hexane-ethyl acetate, 10:3, $R_f$=0.5). Stored at 28.4 mCi/ml in hexane-ethyl acetate (8:2) at 25° C., the radiochemical purity as determined by TLC as above is unchanged after 4 months.

Example 4

Synthesis of [Methyl Ester-$^3$H]Carfentanil (VI) with [methyl-$^{12}C^3$H]Methyl Para-nitrobenzenesulfonate (V)

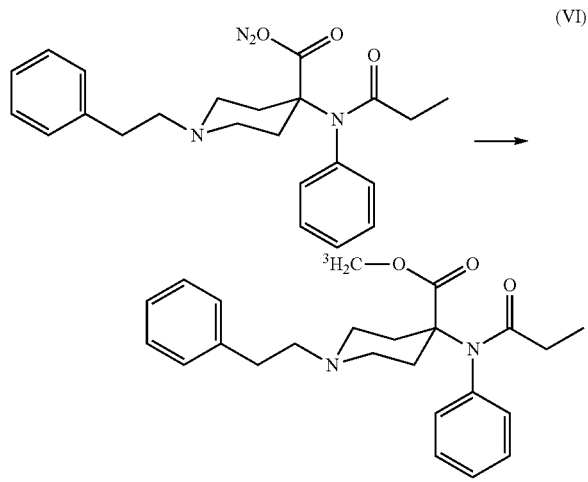

(VI)

400 mCi (0.005 mmol) of [methyl-$^3$H]methyl para-nitrobenzenesulfonate (V) and 1.5 mg (0.0036 mmol) of carfentanil sodium salt are stirred in 0.2 ml of anhydrous DMF at room temperature overnight. TLC of the reaction (Whatman LK6DF, chloroform-methanol-ammonium hydroxide, 100:2:1) show only product and unreacted nosylate. Analysis by HPLC on ODS show that 91% of the activity coeluted with cold standard. A portion is purified on HPLC (Zorbax SB-C18, acetonitrile-0.1% trifluoroacetic acid, gradient) to give [Methyl ester-$^{12}C^3$H]carfentanil (VI). The specific activity is determined to be 80.0 Ci/mmol by mass spectral analysis, and the radiochemical purity determined by HPLC as above is 99%.

Example 5

Preparation of [Methyl-$^3$H]-Raclopride (VII)

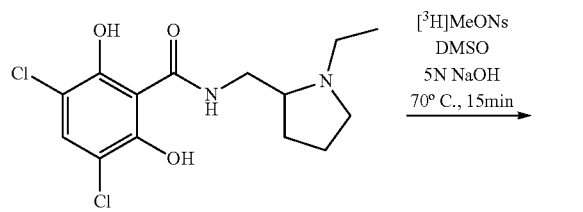

(VII)

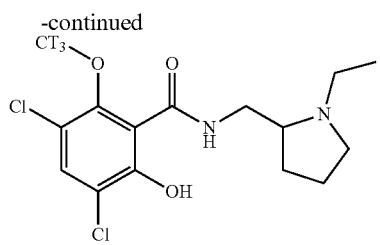

Raclopride is prepared at 80.5 Ci/mmol by heating the reaction to 70° C. in DMSO. The methyl nosylate (V) is able to be dispensed by volume, and the solvent removed to leave the reagent ready for use in the reaction vessel. In the methylation of the raclopride precursor, the stoichiometry of the reaction is able to be carefully controlled to minimize dimethylation.

Example 6

Methylating Comparison $C^3H_3I$ and Methyl Nosylate (V)

The methylating ability of methyl iodide vs. methyl nosylate is compared in a competition experiment. The potassium salt of 2-naphthylacetic acid is stirred in dimethyl formamide with one equivalent of cold methyl iodide and one equivalent of tritiated methyl nosylate (V). The purified material is determined to be 86 Ci/mmol. In this experiment, the nucleophile had been preferentially methylated by the tritiated methyl nosylate (V) with only a small fraction reacting instead with the unlabeled methyl iodide.

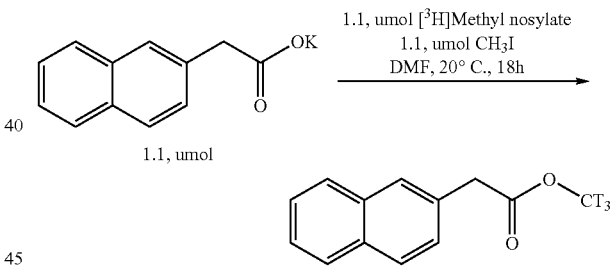

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:
1. An isotopically labeled reagent comprising:
a compound having a formula

$$R^1\text{—}SO_2O\text{—}{}^aC^3H_3$$

where a in each occurrence is independently a carbon atomic mass number of between 11 and 14 inclusive, where $R^1$ is a substituent containing aryl where the substituent is selected from the group consisting of: alkyl, amino, cycloalkyl, halo, nitro, cyano, —$OR^2$, acyl, and —$COOR^3$.

2. The reagent of claim 1 wherein said substituent is para-$NO_2$—$C_6H_4$—.

3. The reagent of claim 1 wherein said substituent is para-$CH_3$—$C_6H_4$—.

* * * * *

UNITED STATES PATENT AND TRADEMARK OFFICE
CERTIFICATE OF CORRECTION

| | |
|---|---|
| PATENT NO. | : 8,058,464 B2 |
| APPLICATION NO. | : 10/559047 |
| DATED | : November 15, 2011 |
| INVENTOR(S) | : Pounds |

It is certified that error appears in the above-identified patent and that said Letters Patent is hereby corrected as shown below:

Column 7, line 27 delete "$^3H$" insert --$^2H$--.

Signed and Sealed this
Twenty-ninth Day of May, 2012

David J. Kappos
*Director of the United States Patent and Trademark Office*